United States Patent [19]
Jacquesy et al.

[11] Patent Number: 5,620,985
[45] Date of Patent: Apr. 15, 1997

[54] **ANTIMITOTIC BINARY ALKALOID DERIVATIVES FROM *CATHARANTHUS ROSEUS***

[75] Inventors: Jean-Claude Jacquesy, Buxerolles; Jacques Fahy, Labruguiere; Christian Berrier, Chasseneuil-du-Poitou; Dennis Bigg, Castres; Marie-Paule Jouannetaud; Fabien Zunino, both of Poitiers; Anna Kruczynski, Castres, all of France; Robert Kiss, Wauthier-Braine, Belgium

[73] Assignee: Pierre Fabre Medicament, Boulogne, France

[21] Appl. No.: 578,669

[22] PCT Filed: Jul. 19, 1994

[86] PCT No.: PCT/FR94/00898

§ 371 Date: Jan. 19, 1996

§ 102(e) Date: Jan. 19, 1996

[87] PCT Pub. No.: WO95/03312

PCT Pub. Date: Feb. 2, 1995

[30] Foreign Application Priority Data

Jul. 21, 1993 [FR] France ................... 93 08948

[51] Int. Cl.$^6$ ................ C07D 519/04; A61K 31/475
[52] U.S. Cl. ................................. 514/283; 540/478
[58] Field of Search .............. 540/478; 546/199; 514/283

[56] References Cited

U.S. PATENT DOCUMENTS

| | | | |
|---|---|---|---|
| 4,110,330 | 8/1978 | Barnett et al. | 540/478 |
| 4,203,898 | 5/1980 | Cullinan et al. | 540/478 |
| 4,307,100 | 12/1981 | Langlois et al. | 514/214 |
| 4,320,058 | 3/1982 | Miller et al. | 540/478 |
| 4,746,665 | 5/1988 | Szantay et al. | 514/283 |
| 4,769,453 | 9/1988 | Potier et al. | 540/478 |

*Primary Examiner*—C. Warren Ivy
*Assistant Examiner*—Lyman H. Smith
*Attorney, Agent, or Firm*—The Firm of Gordon W. Hueschen

[57] ABSTRACT

Novel fluorinated derivatives of the vinblastine and vinorelbine family of general formula (1),

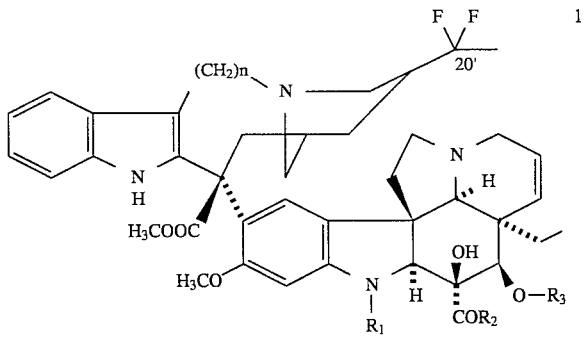

wherein the symbols have the meanings indicated in the Specification and Claims, and the therapeutically-acceptable salts of these molecules, as well as pharmaceutical compositions thereof. The invention also concerns the application of said compounds in the treatment of a cancer pathology and their methods of preparation.

13 Claims, No Drawings

ANTIMITOTIC BINARY ALKALOID DERIVATIVES FROM *CATHARANTHUS ROSEUS*

This application is a 35 U.S.C. 371 National Stage filing of PCT FR94/00898 published as WO95/03312 on Feb. 2, 1995.

Antimitotic alkaloids extracted from *Catharanthus roseus*, which have been used in anticancer chemotherapy for more than thirty years, are mainly represented by vinblastine (R=CH₃) and vincristine (R=CHO).

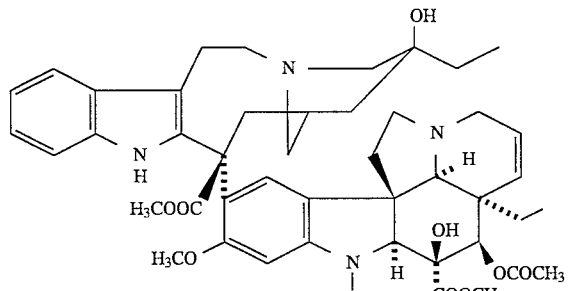

VINBLASTINE (R = CH₃
VINCRISTINE (R = CHO)

A great number of semi-synthetic derivatives have since been studied both chemically and pharmacologically, and only a few have reached the stage of clinical studies [O. Van Tellingen, J. H. M. Sips, J. H. Beijnen, A. Bult and W. J. Nooijen, Anticancer Research, 12, 1699–1716 (1992)].

Only two additional products, obtained by semi-synthesis, have been marketed worldwide: vindesine by the E. Lilly Laboratories in 1983, and vinorelbine by the Pierre Fabre Laboratories in 1989.

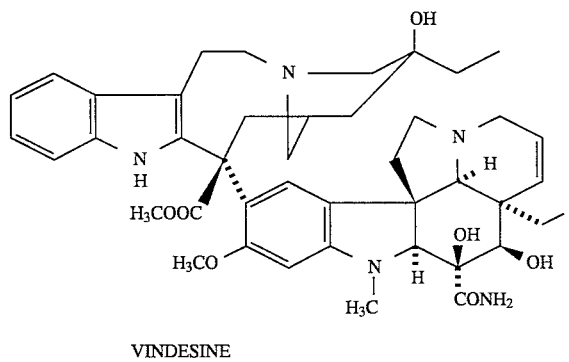

VINDESINE

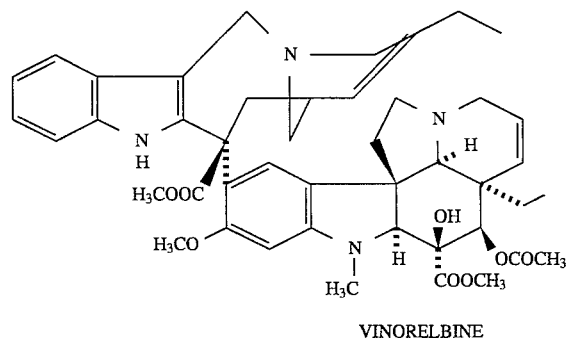

VINORELBINE

Within the context of our program of research into novel antimitotic agents, we have discovered, surprisingly, that the binary alkaloids of the vinblastine and vinorelbine family react selectively in "superacid", type media, in order to lead to novel products, fluorinated on sites which are inaccessible by the standard chemical routes.

The subject of the present invention is novel chemical compounds derived from binary alkaloids from *Catharanthus roseus*, their preparation and their therapeutic application.

The compounds of the invention possess the general formula I:

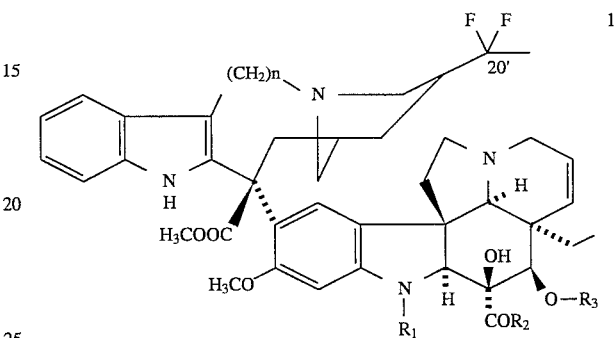

in which:

n is equal to 1 or 2, $R_1$ represents a methyl group or a formyl group, $R_2$ represents a methoxy group or an amino group, $R_3$ represents a hydrogen atom or an acetyl group.

The invention also relates to the salts of the compounds of formula 1 with pharmaceutically acceptable inorganic or organic acids. The acid employed may be, by way of a non-limiting example, sulfuric acid or tartaric acid.

The invention equally relates to the mixtures of diastereoisomers corresponding to configurations of carbon 20' of the compounds of general formula 1, as well as to their mixture in all proportions.

The derivatives of the invention are prepared by reaction of a compound of general formula 2 in superacid medium, originating from the combination of a Bronsted acid such as hydrofluoric acid HF and a Lewis acid such as antimony pentafluoride $SbF_5$, in the presence of a halogenating reagent such as bromine, a hypochlorite such as calcium hypochlorite or an N-halo imide such as N-chlorosuccinimide or N-bromosuccinimide.

The compounds of general formula 2 possess the structure described below:

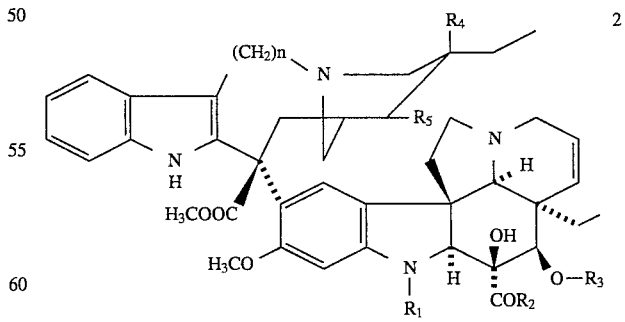

in which:

n, $R_1$, $R_2$ and $R_3$ are defined as above, $R_4$ represents a hydroxyl group, and $R_5$ represents a hydrogen atom; or alternatively $R_4$ and $R_5$ together form a double bond.

The reaction is carried out at a temperature between −60° C. and −15° C. in Teflon vessels according to the following scheme:

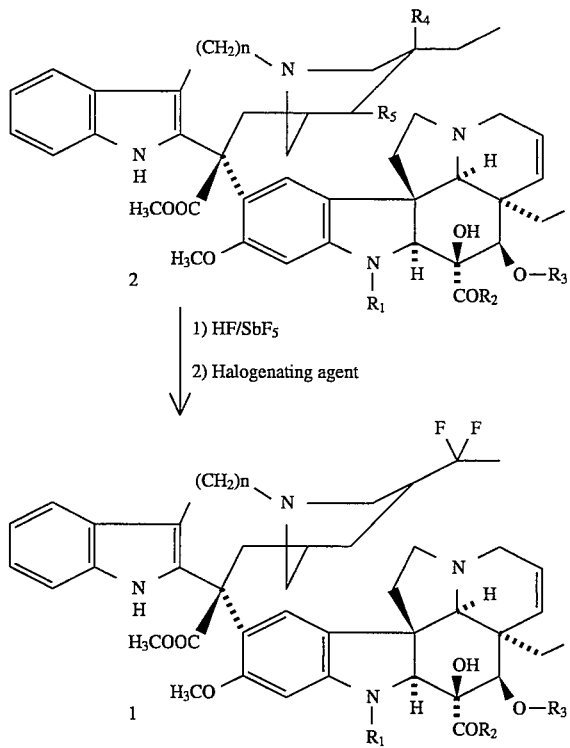

The compounds of general formula 1 where $R_3=H$ may also be prepared by hydrolysis of the ester function of the compounds 1 where $R_3=COCH_3$. This step is preferably carried out in methanol in the presence of sodium methoxide, according to the following scheme:

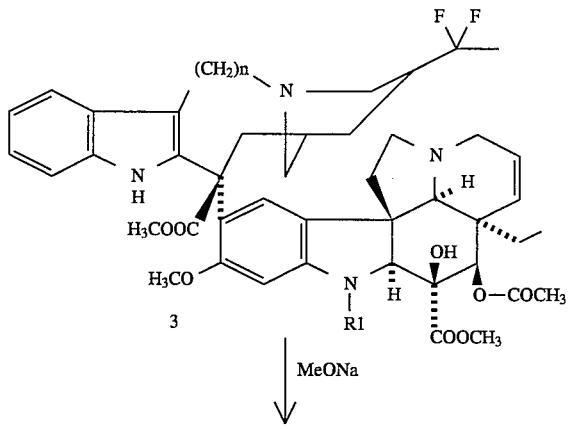

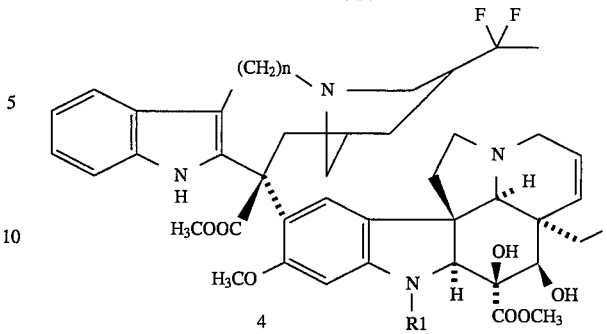

where 3 corresponds to the compound 1 when $R_3=COCH_3$, and 4 corresponds to the compound 1 when $R_3=H$.

The examples which follow illustrate the invention without, however, limiting the scope thereof.

The spectroscopic characteristics (IR, NMR, high resolution mass confirm the structure of the compounds obtained according to the invention.

The products are described using biogenetic numbering [J. Lemen and W. I. Taylor, Experientia, 21, 508 (1965)].

EXAMPLE 1

19',19'-difluoro 15',20'-dihydrovinorelbine 1.
(n=1, $R_1=CH_3$, $R_2=OCH_3$, $R_3=COCH_3$)

To a solution of 33.75 g (156 mmol) of antimony pentafluoride in 33.75 g (1690 mmol) of anhydrous hydrofluoric acid contained in a 125 ml Teflon flask and cooled to −50° C. are added, with magnetic stirring, 2.69 g (2.5 mmol) of vinorelbine ditartrate 2 (n=1, $R_1=CH_3$, $R_2=OCH_3$, $R_3=COCH_3$, $R_4$ and $R_5=$double bond), followed by 0.48 g (2.7 mmol) of N-bromosuccinimide. The mixture is kept stirring at −50° C. for 20 minutes.

The crude reaction mixture is then poured rapidly onto one liter of (water+ice) mixture to which is added 80 g of sodium carbonate so as to prevent the mixture from heating up. 15 ml of acetone are then added in order to promote the extraction, which is carried out with 3 times 500 ml of dichloromethane. The organic phase is separated out and dried over $MgSO_4$ and the solvent is evaporated off under reduced pressure.

The residue obtained is then purified by chromatography on a column of silica eluted with a ($CHCl_3$/EtOH) mixture whose composition changes gradually from (99/1) to (90/10). 0.52 g (25%) of 19',19'-difluoro 15',20'-dihydrovinorelbine is thus recovered.

This compound is dissolved in 3 ml of absolute EtOH and then salified by addition of 1.8 ml of a 2% solution of concentrated sulfuric acid in EtOH. The mixture is then added dropwise, with vigorous stirring, to 20 ml of ethyl ether cooled in an ice bath. The white, hygroscopic precipitate obtained is filtered off and dried under vacuum.

$C_{45}H_{54}F_2N_4O_8 \cdot H_2SO_4$: 915.01 Melting point: >260° C. IR (KBr): 3437, 2953, 1740, 1618, 1460, 1435, 1234, 1116, 1043 cm-1. High resolution mass spectrum (HRFABMS): for $C_{45}H_{55}F_2N_4O_8$ (MH+): Calculated: 817.3987 Measured: 817.3999 $^1$H NMR (200 MHz, CDCl$_3$) on the free base: 0.70 (3 H, t, J=7.4 Hz, $C_{18}\underline{H}$); 1.18–1.45 (4 H, broad m); 1.63 (3 H, t, $^J$HF=18.9 Hz, $C_{18}\underline{H}$); 1.53–1.94 (4 H, broad m); 2.10 (3 H, s, COC$\underline{H}_3$); 2.30–2.38 (2 H, broad m); 2.55 (1 H, s, $C_{21}\underline{H}$); 2.63–2.79 (2 H, broad m); 2.72 (3 H, s, N—C$\underline{H}_3$); 2.90–3.12 (2 H, m); 3.18–3.40 (4 H, broad m); 3.71 (3 H, s, OC$\underline{H}_3$); 3.73 (1 H, s, $C_2\underline{H}$); 3.79 (3 H, s, OC$\underline{H}_3$); 3.82 (3 H, s, OC$\underline{H}_3$); 4.45 (1 H, d J=11.8 Hz, $C_6,\underline{H}'$); 4.55 (1 H, d, J=11.8 Hz, $C_6$, H'); 5.28 (1 H, d, J=10.2 Hz, $C_{15}\underline{H}$); 5.41 (1 H, s, $C_{17}\underline{H}$); 5.86 (1 H, dd, J=10.2/3.8 Hz, $C_{14}\underline{H}$); 6.09 (1 H, s, $C_{12}\underline{H}$); 6.35 (1 H, s, $C_9\underline{H}$); 7.16 (3 H, m, $C_{10},\underline{H}, C_{11},\underline{H}$ and $C_{12},\underline{H}$); 7.71 (1 H, m, $C_9,\underline{H}$); 8.42 (1 H, exch., $C_{16}O\underline{H}$); 9.86 (1 H, exch., N$\underline{H}$) .

EXAMPLE 2

19',19'-difluoro 15',20'-dihydrovinorelbine 1
(n=1, $R_1$=CH$_3$, $R_2$=OCH$_3$, $R_3$=COCH$_3$)

This derivative is obtained according to the procedure described in Example 1, replacing the N-bromosuccinimide by N-chlorosuccinimide during the treatment in superacid medium.

The react ion time in superacid medium is 20 minutes at −50° C.

The physicochemical and spectroscopic characteristics of the isolated product are identical to those of the compound obtained in Example 1.

EXAMPLE 3

19',19'-difluoro 15',20'-dihydrovinorelbine 1
(n=1, $R_1$=CH$_3$, $R_2$=OCH$_3$, $R_3$=COCH$_3$)

This derivative is obtained according to the procedure described in Example 1, adding 0.7 equivalent bromine relative to the vinorelbine in place of the N-bromosuccinimide during the treatment in superacid medium.

The reaction time in superacid medium is 15 minutes at −30° C.

The physicochemical and spectroscopic characteristics of the isolated product are identical to those of the compound obtained in Example 1.

EXAMPLE 4

19',19'-difluoro 15',20'-dihydrovinorelbine 1
(n=1, $R_1$=CH$_3$, $R_2$=OCH$_3$, $R_3$=COCH$_3$)

This derivative is obtained according to the procedure described in Example 1, replacing the N-bromosuccinimide by calcium hypochlorite during the treatment in superacid medium.

The reaction time in superacid medium is 20 minutes at −50° C.

The physicochemical and spectroscopic characteristics of the isolated product are identical to those of the compound obtained in Example 1.

EXAMPLE 5

20'-deoxy 19',19'-difluorovinblastine 1
(n=2, $R_1$=CH$_3$, $R_2$=OCH$_3$, $R_3$=COCH$_3$)

This derivative is obtained according to the procedure described in Example 1, using vinblastine sulfate of formula 2 (n=2, $R_1$=CH$_3$, $R_2$=OCH$_3$, $R_3$=COCH$_3$, $R_4$=OH and $R_5$=H) in place of the vinorelbine ditartrate.

The reaction time in superacid medium is 15 minutes at −30° C.

$C_{46}H_{56}F_2N_4O_8 \cdot H_2SO_4$; 929.04 Melting point: 180°–186° C. (dec.) IR (KBr): 3453, 2957, 1741, 1618, 1512, 1460, 1439, 1371, 1226, 1037, 900 cm$^{-1}$ High resolution mass spectrum (HRFABMS): for $C_{46}H_{57}F_2N_4O_8$ (MH+): Calculated: 831.4144 Measured: 831.3979 $^1$H NMR (200 MHz, CDCl$_3$) on the free base: 0.81 (3 H, t J=7.4 Hz, $Cl_8\underline{H}$); 1.23–1.60 (7 H, broad m); 1.55 (3 H, t, JHF=19.2 Hz, $C_{18},\underline{H}$); 2.12 (3 H, s, COC$\underline{H}_3$); 2.41 (5 H, broad m); 2.66 (1 H, s, $C_{21}\underline{H}$); 2.63–2.88 (2 H, broad m); 2.73 (3 H, s, N—C$\underline{H}_3$); 3.22 (8 H, broad m); 3.64 (3 H, s, OC$\underline{H}_3$); 3.76 (1 H, s, $C_2\underline{H}$); 3.80 (3 H, s, OC$\underline{H}_3$); 3.82 (3 H, s, OC$\underline{H}_3$); 5.32 (1 H, d, J=10.2 Hz, $C_{15}$ $\underline{H}$); 5.45 (1 H, s, $C_{17}\underline{H}$); 5.88 (1 H, dd, J=10.2/3.8 Hz, $C_{14}$ $\underline{H}$); 6.11 (1 H, s, $C_{12}\underline{H}$); 6.57 (1 H, s, $C_9\underline{H}$); 7.16 (3 H, m, $C_{10},\underline{H}, C_{11},\underline{H}$ and $C_{12},\underline{H}$); 7.49 (1 H, m, $C_9,\underline{H}$); 8.04 (1 H, exch., $C_{16}O\underline{H}$); 9.85 (1 H, exch., N$\underline{H}$).

EXAMPLE 6

20'-deoxy 19',19'-difluorovinblastine 1
(n=2, $R_1$=CH$_3$, $R_2$=OCH$_3$, $R_3$=COCH$_3$)

This derivative is obtained according to the procedure described in Example 1, using 15',20'-anhydrovinblastine of formula 2 (n=2, $R_1$=CH$_3$, $R_2$=OCH$_3$, $R_3$=COCH$_3$, $R_4$ and $R_5$=double bond) in place of the vinorelbine ditartrate.

The reaction time in superacid medium is 15 minutes at −30° C.

The physicochemical and spectroscopic characteristics of the isolated product are identical to those of the derivative obtained in Example 5.

EXAMPLE 7

20'-deoxy 19',19'-difluorovindesine 1
(n=2, $R_1$=CH$_3$, $R_2$=NH$_2$, $R_3$=H)

This derivative is obtained according to the procedure described in Example 1, using vindesine 2 (n=2, $R_1$=CH$_3$, $R_2$=NH$_2$, $R_3$=H, $R_4$=OH, $R_5$=H) in place of the vinorelbine ditartrate.

The reaction time in superacid medium is 15 min at −30° C.

$C_{43}H_{53}F_2N_5O_6$: 773.92 Melting point: 186° C. (dec.) IR (KBr): 3458, 2924, 2851, 1734, 1686, 1616, 1508, 1458, 1232, 1037 cm-1 $^1$H NMR (200 MHz, CDCl$_3$+D$_2$O): 0.94 (3 H, t, J=7.6 Hz, $C_{18}\underline{H}$); 1.18–1.74 (4 H, broad m); 1.55 (3 H, t, $^J$HF=19.0 Hz, $C_{18},\underline{H}$); 2.07–2.55 (4 H, broad m); 2.62 (1 H, s, $C_{21}\underline{H}$); 2.64–2.89 (4 H, broad m); 2.90 (3 H, s, N—C $\underline{H}_3$); 3.10–3.40 (10 H, broad m); 3.48 (1 H, s, $C_2\underline{H}$); 3.62 (3 H, s, OC$\underline{H}_3$); 3.80 (3 H, s, OC$\underline{H}_3$); 4.14 (1 H, s, $C_{17}\underline{H}$); 4.75 broad m, HOD); 5.58 (1 H, d, J=10.8 Hz, $C_{15}\underline{H}$); 5.82 (1 H, dd, J=10.8/3.5 Hz, $C_{14}\underline{H}$); 6.11 (1 H, s, $C_{12}\underline{H}$); 6.55 (1 H, s, $C_9\underline{H}$); 7.18 (3 H, m, $C_{10},\underline{H}; C_{11},\underline{H}$ and $C_{12},\underline{H}$); 7.50 (1 H, d, J=7.1 Hz, $C_9,\underline{H}$).

EXAMPLE 8

20'-deoxy 19',19'-difluorovindesine 1
(n=2, $R_1$=CH$_3$, $R_2$=NH$_2$, $R_3$=H)

This derivative is obtained according to the procedure described in Example 1, using 15',20'-anhydrovindesine 2 (n=2, $R_1$=CH3, $R_2$=NH2, $R_3$=H, $R_4$ and $R_5$=double bond) in place of the vinorelbine ditartrate. The reaction in superacid medium is 15 min at −30° C.

The physicochemical and spectroscopic characteristics of the isolated product are identical to those of the derivative obtained in Example 7.

EXAMPLE 9

$N_a$-demethyl $N_a$-formyl 19',19'-difluoro 15',20'-dihydrovinorelbine 1
(n=1, $R_1$=CHO, $R_2$=OCH$_3$, $R_3$=COCH$_3$)

This derivative is obtained according to the procedure described in Example 1, using $N_a$-demethyl $N_a$-formylvinorelbine sulfate of formula 2 (n=1, $R_1$=CHO, $R_2$=OCH$_3$, $R_3$=COCH$_3$, $R_4$ and $R_5$=double bond) in place of the vinorelbine ditartrate.

The reaction time in superacid medium is 15 minutes at −30° C.

$C_{45}H_{52}F_2N_4O_9$: 830.89 Melting point: >260° C. (dec.) IR (KBr): 3441, 2951, 1745, 1686, 1456, 1371, 1232, 1033, 908, 736 cm$^{-1}$ $^1$H NMR (200 MHZ, CDCl$_3$): 0.73 (3 H, t, J=7.5 Hz, C$_{18}$H); 0.95–1.42 (3 H, broad m); 1.52–1.91 (4 H, broad m); 1.62 (3 H, t, $^J$HF=18.8 Hz, C$_{18}$H); 2.06 and 2.09 (3 H, 2s, COCH$_3$); 2.21, 2.29 (2 H, m); 2.59–3.11 (6 H, broad m); 3.32 (4 H, m); 3.72 (3 H, s, OCH$_3$); 3.78 and 3.80 (3 H, 2s, OCH$_3$); 3.91 (3 H, s OCH$_3$); 4.42 (1 H, d, J=11.5 Hz, C$_6$H); 4.52 (1 H, d, J=11.5 Hz, C$_6$, H) ; 4.49 and 4.72 (1 H, 2s, C$_2$H); 5.17 and 5.20 (1 H, 2s, C$_{17}$H); 5.37 (1 H, d, J=10.7 Hz, C$_{15}$H); 5.88 (1H, m, C$_{14}$H); 6.63 and 6.67 (1 H, 2s, C$_9$H); 6.73 and 7.79 (1 H, 2s, C$_{12}$H); 7.18 (3 H, m, C$_{10}$, H, C$_{11}$,H and C$_{12}$,H); 7.70 (1 H, m, C$_9$,H); 8.43 (1 H exch., C$_{16}$OH); 8.16 and 8.75 (1 H, 2s, CHO); 9.35 (1 H exch., N H).

EXAMPLE 10

20'-deoxy 19',19'-difluorovincristine 1
(n=2, $R_1$=CHO, $R_2$=OCH$_3$, $R_3$=COCH$_3$)

This derivative obtained according to the procedure described in Example 1, using vincristine sulfate of formula 2 (n=2, $R_1$=CHO, $R_2$=OCH$_3$, $R_3$=COCH$_3$, $R_4$=OH and $R_5$=H) in place of the vinorelbine ditartrate.

The reaction time in superacid medium is 15 minutes at −30° C.

$C_{46}H_{54}F_2N_4O_9$: 844.92 Melting point: 228°–233° C. (dec.) IR (KBr): 3462, 2951, 1743, 1684, 1597, 1496, 1456, 1369, 1232, 1033 cm-1. $^1$H NMR (200 MHz, CDCl$_3$): 0.84 (3 H, t, J=7.5 Hz, C$_{18}$H); 1.20–1.77 (6 H, broad m); 1.53 (3 H, t, $^J$HF=19.0 Hz, C$_{18}$,H); 2.05–2.59 (6 H, broad m) ; 2.07 and 2.09 (3 H, 2s COCH$_3$); 2.74, 2.92 (1 H, broad m); 2.89 (1 H, s, C$_{21}$H); 3.10–3.53 (5 H, broad m); 3.69 (3 H, s, OCH$_3$); 3.72 and 3.79 (3 H, 2s, OCH$_3$); 3.90 (3 H, s, OCH$_3$); 4.51 and 4.74 (1 H, 2s, C$_2$H); 5.21 and 5.25 (1 H, 2s, C$_{17}$H); 5.41 (1 H, d, J=10.2 Hz, C$_{15}$H); 5.93 (1 H, dd, J=10.2/3.8 Hz, C$_{14}$H); 6.81 and 6.85 (1 H, 2s, C$_9$H); 6.90 and 7.76 (1 H, 2s, C$_{12}$H); 7.18 (3 H, m, C$_{10}$,H, C$_{11}$,H, C$_{12}$, H); 7.52 (1 H, d, J=7.0 Hz, C$_9$,H); 8.07 (1 H, exch., C$_{16}$O H); 8.17 and 8.77 (1 H, 2s, CHO); 9.70 (1 H, exch., NH).

EXAMPLE 11

17-deacetyl 19',19'-difluoro 15',20'-dihydrovinorelbine 1
(n=1, $R_1$=CH$_3$, $R_2$=OCH$_3$, $R_3$=H)

To a solution of 200 mg (0.24 mmol) of 19',19-difluoro 15',20'-dihydrovinorelbine 1 (n=1, $R_1$=CH$_3$, $R_2$=OCH$_3$, $R_3$=COCH$_3$) , obtained in Example 1, in 10 ml of dry methanol under a nitrogen atmosphere and with stirring, are added 130 mg (2.40 mmol) of sodium methoxide. After 12 hours, the mixture is poured into 100 ml of water+ice and then extracted with 3 times 20 ml of dichloromethane. The organic phase is separated out, dried over MgSO$_4$, filtered and evaporated. The residue obtained is purified by chromatography on a column of silica eluted with a hexane/EtOAc/MeOH mixture (4/2/1). 134 mg (72%) of 17-deacetyl 19',19'-difluoro 15',20'-dihydrovinorelbine are thus recovered in the form of a whitish powder.

$C_{43}H_{52}F_2N_4O_7$: 774.90 Melting point: 240°–245° C. (dec.) IR (KBr): 3445, 2947, 1736, 1616, 1504, 1460, 1433, 1234, 1049, 904, 742 cm-1 High resolution mass spectrum (HRFABMS): for $C_{43}H_{53}F_2N_4O_7$ (MH+): Calculated: 775.3882 Measured: 775.3759 $^1$H NMR (200 1/11 Hz, CDCl$_3$): 0.86 (3 H, t J=7.4 Hz, Cl$_8$H); 0.96–1.42 (4 H, broad m); 1.63 (3 H, t, $^J$HF=19.0 Hz, C$_{18}$,H); 1.53–2.05 (4 H, m broad); 2.05–3.48 (12 H, broad m); 2.50 (1 H, s, C$_{21}$H); 2.77 (3 H, s, N—CH$_3$); 3.70 (3 H, s, OCH$_3$); 3.81 (3 H, s, OC H$_3$); 3.84 (3 H, s, OCH$_3$); 4.01 (1 H, s, C$_{17}$H); 4.51 (2 H, broad s, C$_6$,H); 5.70 (1 H, d, J=10.6 Hz, C$_{15}$H); 5.85 (1 H, dd, J=10.6/3.8 Hz, C$_{14}$H); 6.10 (1 H, s, C$_{12}$H); 6.35 (1 H, s, C$_9$H); 7.18 (3 H, m, C$_{10}$,H, C$_{11}$,H, C$_{12}$,H); 7.72 (1 H, m, C$_9$, H); 8.42 (1 H, exch., C$_{16}$OH); 9.50 (1 H, exch., NH) .

EXAMPLE 12

17-deacetyl-20'-deoxy 19',19 '-difluorovinblastine 1
(n=2, $R_1$=CH$_3$, $R_2$=OCH$_3$, $R_3$=H)

This derivative is obtained according to the procedure described in Example 11, replacing the 19',19'-difluoro 15',20'-dihydrovinorelbine 1 (n=1, $R_1$=CH$_3$, $R_2$=OCH$_3$, $R_3$=COCH$_3$) by 20'-deoxy 19',19'-difluorovinblastine 1 (n=2, $R_1$=CH$_3$, $R_2$=OCH$_3$, $R_3$=COCH$_3$) obtained in Example 5. After purification, the 17-deacetyl 20'-deoxy 19',19'-difluorovinblastine 1 (n=2, $R_1$=CH$_3$, $R_2$=OCH$_3$, $R_3$=H) is salified by addition of one equivalent of tartaric acid.

$C_{44}H_{54}F_2N_4O_7 \cdot C_4H_6O_6$: 939.02 Melting point: 180°–185° C. (dec.) IR (KBr): 3447, 2968, 1734, 1616, 1506, 1460, 1234, 1122, 744 cm-1 High resolution mass spectrum (HRFABMS): for $C_{44}H_{55}F_2N_4O_7$ (MH+): Calculated: 789.4038 Measured: 789.4022 $^1$H NMR (200 MHz, CDCl$_3$): 0.95 (3 H, t J=7.4 Hz, C$_{18}$H); 1.18–1.74 (4 H, broad m); 1.53 (3 H, t, $^J$HF=19.0 Hz, C$_{18}$,H); 2.07–2.55 (4 H, broad m); 2.63 (1 H, s, C$_{21}$H); 2.64–2.89 (4 H, broad m); 2.77 (3 H, s, N—CH$_3$); 3.10–3.52 (11 H, broad m); 3.62 (3 H, s, OC H$_3$); 3.72 (1 H, s, C$_2$H); 3.81 (3 H, s, OCH$_3$); 3.85 (3 H, s, OCH$_3$); 4.07 (1 H, s, C$_{17}$H); 5.75 (1 H, d, J=10.8 Hz, C$_{15}$ H); 5.86 (1 H, dd, J=10.8/3.5 Hz, C$_{14}$H); 6.11 (1 H, s, C$_{12}$ H); 6.61 (1 H, s, C$_9$H); 7.12 (3 H, m, C$_{10}$,H, C$_{11}$,H, C$_{12}$, H); 7.51 (1 H, d, J=7.1 Hz, C$_9$,H); 8.01 (1 H, exch., C$_{16}$O H); 9.30 (1 H, exch., NH).

The compounds of the invention were subjected to pharmacological trials which demonstrated their advantage as substances having therapeutic activity. Thus, the cytotoxic activity of the products was evaluated using the MTT test [T. Mosman, *J. Immunol. Method*, 65, 55 (1983)] on various tumor cell lines. The MTT test is based on the capacity which living cells have to reduce, by the action of their mitochondrial enzymes, a yellow tetrazolium salt to a violet-blue compound, formazan, which may be measured by spectrophotometry after dissolution in dimethyl sulfoxide. The amount of formazan formed (and consequently the intensity of the color obtained) is directly proportional to the number of living cells present in the culture medium at the time of the test. The lines used are of human origin, and are marketed by the American Type Cell Collection (ATCC), the reference body for the supply of standardized strains.

| Line | ATCC code | Origin of tumor |
|---|---|---|
| MCF-7 | HTB22 | breast |
| T47D | HTB133 | breast |
| J82 | HTB1 | bladder |
| T24 | HBT4 | bladder |

The experimental procedure used is essentially that described by C. Carmichael, W. G. De Graff, A. F. Gazdor, D. Minna, and B. Mitchell [Cancer Res., 47, 936 (1987)].

The results are expressed in the form of a percentage inhibition of growth relative to the controls.

Table 1 gives, by way of example, the results obtained for certain derivatives of the invention at a concentration of 1 µg/ml.

| Product of the Example | Percentage inhibition of growth | | | |
|---|---|---|---|---|
| | MCF-7 | T47 | J82 | T24 |
| 1 | 68 | 44 | 45 | 70 |
| 5 | 36 | 27 | 15 | 50 |
| 11 | 45 | 30 | 60 | 51 |
| 12 | 36 | 27 | 0 | 72 |
| VINORELBINE | 50 | 16 | 14 | 62 |

Like the antitumor alkaloids from *Catharanthus roseus*, the products prepared according to the invention are mitotic spindle poisons.

This property was confirmed by measuring the inhibition of polymerization of tubulin into microtubules in the presence of the compounds of the invention, according to the method described by R. C. Weisenberg (Science 177, 1196–7, 1972). The results are expressed as a concentration of product which causes 50% inhibition of the polymerization. This phenomenon is readily monitored and quantified via the variations in optical density.

By way of example, Table 2 shows the results obtained with a few derivatives prepared according to the invention:

| Product of the Example | $IC_{50}$ (µM) |
|---|---|
| 1 | 2.50 |
| 5 | 8.9 |
| 11 | 2.9 |
| 12 | 4.2 |
| VINBLASTINE | 1.9 |

The antitumor properties of the products of the invention were confirmed by in vivo tests, in particular on the model of mammalian MXT adenocarcinoma, which is a solid tumor that is particularly insensitive to anticancer agents [C. S. Watson, D. Medina, J. H. Clark, *Cancer Res.*, 37, 3344 (1977); W. T. Bradher and C. A. Claridge, "Antineoplastic Agents", Wiley-Interscience (1984); T. W. Redding and A. V. Schally, *Proc. Natl. Acad. Sci. U.S.A.*, 80, 1459 (1983)].

In this model, mice of type B6D2F1 are grafted by injection (subcutaneous) of a tumor fragment of about 10 mm³ originating from an MXT tumor. The test products are administered via the i.p. route starting from the 17th day after the graft. The MXT test provides two types of results: the effect exhibited by the test molecule on tumor growth, and the survival time of the treated animals relative to the control animals (T/C expressed as a percentage).

By way of example, the compound of Example 1 causes a 40% reduction in tumor size relative to the untreated controls, according to a protocol of 9×40 mg/kg, whereas all the derivatives of this chemical family, vinblastine, vincristine, vindesine and vinorelbine, are devoid of activity on this model.

Given their pharmacological properties, the compounds of the present invention may be used in human therapy in the treatment of cancer pathology.

The pharmaceutical preparations containing these active principles may be formulated for oral, intravenous or subcutaneous administration.

We claim:

1. An antimitotic derivative of a binary alkaloid from *Catharanthus roseus* selected from those corresponding to formula 1:

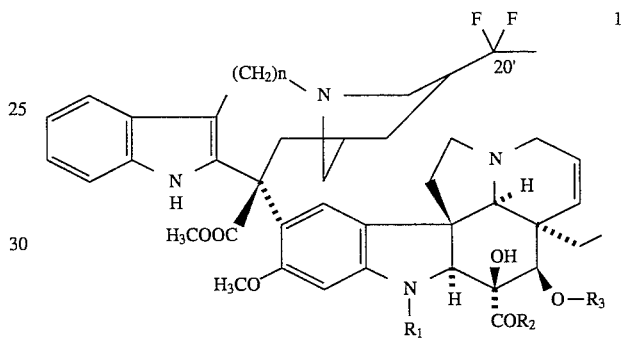

in which:

n is equal to 1 or 2, $R_1$ represents a methyl group or a formyl group, $R_2$ represents a methoxy group or an amino group, $R_3$ represents a hydrogen atom or an acetyl group, as well as the salts thereof with therapeutically-acceptable inorganic or organic acids, and mixtures of the diastereoisomers corresponding to the two configurations of carbon 20' of the compounds in all proportions.

2. A compound of claim 1, characterized in that it is chosen from the group consisting of:

19',19'-difluoro 15',20'-dihydrovinorelbine

20'-deoxy 19',19'-difluorovinblastine

20'-deoxy 19',19'-difluorovindesine $N_a$-demethyl $N_a$-formyl 19',19'-difluoro 15',20'-dihydrovinorelbine 20'-deoxy 19',19'-difluorovincristine 17-deacetyl 19',19'-difluoro 15',20'-dihydrovinorelbine and 17-deacetyl 20'-deoxy 19',19'-difluorovinblastine.

3. Process for the preparation of compound according to claim 1, characterized in that a compound of general formula 2 is reacted in superacid medium, originating from the combination of a Bronsted acid and a Lewis acid, in the presence of a halogenating agent, according to the scheme:

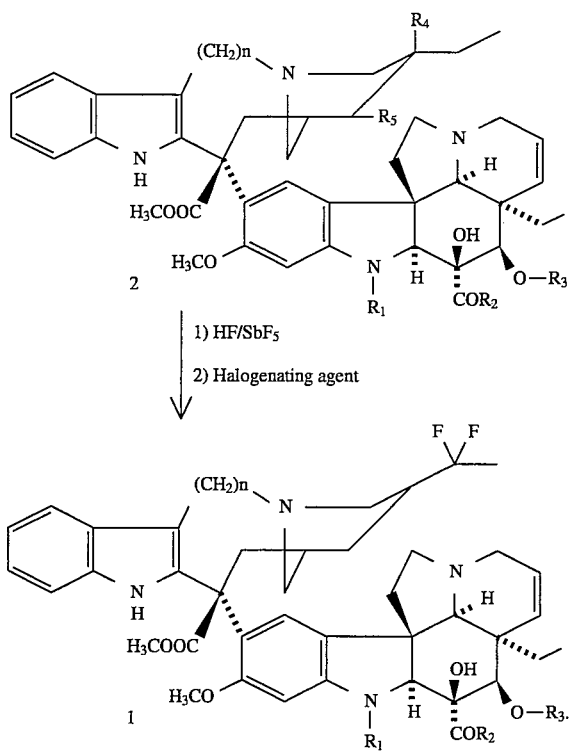

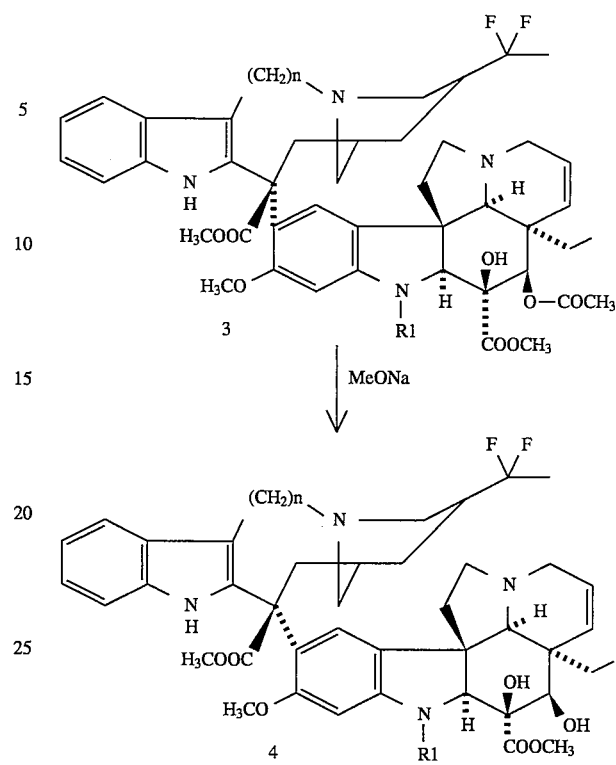

where 3 corresponds to the compound 1 when $R_3$=COCH$_3$, and 4 corresponds to the compound 1 when $R_3$=H.

9. Process for the preparation of compound according to claim 8, characterized in that the hydrolysis is carried out using sodium methoxide in methanol.

10. Pharmaceutical composition, characterized in that it contains, as active principle, at least one compound according to claim 1, combined with a pharmaceutically-acceptable vehicle.

11. Pharmaceutical composition, characterized in that it contains, as active principle, at least one compound according to claim 2, combined with a pharmaceutically-acceptable vehicle.

12. Method of treating a mammal afflicted with a cancer pathology of a type responsive to vinorelbine, vinblastine, or vindesine, for the alleviation thereof, comprising the step of administering to the said mammal an amount of a compound of claim 1 which is effective for said purpose.

13. Method of treating a mammal afflicted with a cancer pathology of a type responsive to vinorelbine, vinblastine, or vindesine, for the alleviation thereof, comprising the step of administering to the said mammal an amount of a compound of claim 2 which is effective for said purpose.

* * * * *

4. Process for the preparation of compound according to claim 3, characterized in that the reaction of a compound of general formula 2 in superacid medium is carried out at a temperature between −60° C. and −15° C.

5. Process for the preparation of compound according to claim 3, characterized in that the halogenating agent is chosen from the group consisting of:

bromine, calcium hypochlorite,

N-chlorosuccinimide,

N-bromosuccinimide.

6. The process of claim 3 wherein the Bronsted acid is hydrofluoric acid.

7. The process of claim 3 wherein the Lewis acid is antimony pentafluoride.

8. Process for the preparation of compound of general formula 1 where $R_3$ represents a hydrogen atom, according to claim 1, characterized in that a compound of general formula 1, where $R_3$ represents an acetyl group, is hydrolyzed according to the scheme:

UNITED STATES PATENT AND TRADEMARK OFFICE
CERTIFICATE OF CORRECTION

PATENT NO. : 5,620,985
DATED : Apr. 15, 1997
INVENTOR(S) : J.C. Jacquesy, J. Fahy, C. Berrier, D. Bigg, M.P. Jouannetaud, F. Zunino, A. Kruczynski, R. Kiss Page 1 of 2

It is certified that error appears in the above-indentified patent and that said Letters Patent is hereby corrected as shown below:

Column 2, line 4: Delete the "," (comma) after "superacid".

Column 5, line 25: "react ion" should read -- reaction --.

Column 10, line 56 (approx.): Insert -- a -- between "of" and "compound".

Column 11, line 31: Insert -- a -- between "of" and "compound".

Column 11, line 36: Insert -- a -- between "of" and "compound".

Column 11, line 43 (approx.): Insert the word -- and -- after "N-chlorosuccinimide,".

UNITED STATES PATENT AND TRADEMARK OFFICE
CERTIFICATE OF CORRECTION

PATENT NO. : 5,620,985
DATED : Apr. 15, 1997
INVENTOR(S) : J.C. Jacquesy, J. Fahy, C. Berrier, D. Bigg, M.P. Jouannetaud, F. Zunino, A. Kruczynski, R. Kiss It is certified that error appears in the above-indentified patent and that said Letters Patent is hereby corrected as shown below:

Column 11, line 49:  Insert -- a -- between "of" and "compound".

Column 12, line 33:  Insert -- a -- between "of" and "compound".

Signed and Sealed this

Eighth Day of July, 1997

Attest:

BRUCE LEHMAN

*Attesting Officer*    *Commissioner of Patents and Trademarks*